US009482605B2

(12) United States Patent
Deards et al.

(10) Patent No.: US 9,482,605 B2
(45) Date of Patent: Nov. 1, 2016

(54) BOND TESTING MACHINE AND CARTRIDGE FOR A BOND TESTING MACHINE COMPRISING A PLURALITY OF TEST TOOLS

(71) Applicant: Nordson Corporation, Westlake, OH (US)

(72) Inventors: Robert Brian Deards, Colchester (GB); Ian Christopher Mayes, Ampthill (GB); Martin Bugg, Ipswich (GB); David T. Lilley, Colchester (GB)

(73) Assignee: Nordson Corporation, Westlake, OH (US)

( * ) Notice: Subject to any disclaimer, the term of this patent is extended or adjusted under 35 U.S.C. 154(b) by 132 days.

(21) Appl. No.: 14/317,525

(22) Filed: Jun. 27, 2014

(65) Prior Publication Data

US 2015/0007668 A1  Jan. 8, 2015

(30) Foreign Application Priority Data

Jul. 3, 2013  (EP) .................................... 13174870

(51) Int. Cl.
*G01N 3/24* (2006.01)
*G01N 3/00* (2006.01)
*G01N 19/04* (2006.01)
*G01N 3/04* (2006.01)
(Continued)

(52) U.S. Cl.
CPC  *G01N 3/24* (2013.01); *G01N 3/00* (2013.01); *G01N 3/04* (2013.01); *G01N 19/04* (2013.01); *G01N 2203/0003* (2013.01); *G01N 2203/0017* (2013.01); *G01N 2203/0025* (2013.01); CPC ......... *G01N2203/0067* (2013.01); *G01N 2203/0296* (2013.01)

(Continued)

(58) Field of Classification Search
CPC .................. G01N 3/00; G01N 19/04; G01N 2203/0003; G01N 2203/0017; G01N 2203/0025; G01N 2203/0067; G01N 2203/0296; G01N 3/04; G01N 3/24; G01N 2203/021; G01N 2203/0044; G01N 2203/0051; G01N 2203/0248; G01N 2203/0286; G01N 2203/0411; G01N 2203/0623; H01L 2224/859; G01R 1/06705; G01R 1/06794; G01R 31/2853
USPC ............ 307/329; 73/842, 788, 841, 862.638, 73/862.584, 827, 852–854, 850, 812, 833; 432/37; 356/244, 231
See application file for complete search history.

(56) References Cited

U.S. PATENT DOCUMENTS 6,078,387 A    6/2000  Sykes
2010/0288012 A1  11/2010  Su et al.
(Continued)

OTHER PUBLICATIONS

Lim E J, Multi-cartridge-type junction bonding force test apparatus for use during semiconductor manufacturig process, has rotation rod module fixed to movable unit that is movably installed in body along perpendicular direction, Nov. 6, 2012, pp. 1-8.*

(Continued)

*Primary Examiner* — Lisa Caputo
*Assistant Examiner* — Brandi Hopkins
(74) *Attorney, Agent, or Firm* — Baker & Hostetler LLP (57) ABSTRACT

A cartridge suitable for use in a bond testing machine includes a plurality of a different test tools. A rotary mechanism is provided and each of the plurality of different test tools is mounted to the rotary mechanism angularly spaced from one another. A drive unit is coupled to the rotary mechanism and is configured to rotate the rotary mechanism to move each of the plurality of different test tools to and from a use position. An air interface receives compressed air from a corresponding air interface on a positioning assembly of the bond testing machine.

28 Claims, 5 Drawing Sheets

(56) References Cited

U.S. PATENT DOCUMENTS

| | | |
|---|---|---|
| 2011/0214507 A1 | 9/2011 | Lilley et al. |
| 2011/0214510 A1* | 9/2011 | Lilley .................. G01N 3/24 73/841 |
| 2012/0204654 A1 | 8/2012 | Sykes |

OTHER PUBLICATIONS

European Patent Office, Partial European Search Report in EP Application No. 13174870, Mar. 3, 2014.

European Patent Office, European Search Report and Written Opinion in EP Application No. 13174870, Apr. 25, 2014.

* cited by examiner

BOND TESTING MACHINE AND CARTRIDGE FOR A BOND TESTING MACHINE COMPRISING A PLURALITY OF TEST TOOLS

FIELD OF THE INVENTION

The present invention relates to a device for testing the strength of electrical bonds on semiconductor devices. In particular, the invention relates to a device that is able to perform different types of tests such as a shear test, a pull test and a push test on electrical bonds.

BACKGROUND TO THE INVENTION

Semiconductor devices are very small, typically from 5 mm×5 mm square to 50 mm×50 mm square, and typically comprise numerous sites for the bonding of electrical conductors to a semiconductor substrate. Each bond consists of a solder ball/bump or copper pillar or wire.

It is necessary to test the bond strength of the bonds, in order to be confident that a particular bonding method is adequate. Because of the very small size of the bonds, tools used to test the bond strength of these bonds must be able to measure very small forces and deflections accurately.

There are several different types of bond tests that are used to test bond strength. For example, shear testing tests the shear strength of a bond by applying a shear force to the side of the bond and shearing the bond off the substrate. Pull testing tests the pull strength of the bond by pulling the bond away from the substrate. In a push test, a force, or load, is applied in the vertical plane directly downward onto a bond.

Machines that perform these tests typically comprise a bond test tool, be it a shear test tool, push test tool or a pull test tool, that can be positioned relative to the bond under test and then either the bond or the tool are moved in order to perform the test, which comprises measuring the force needed to break the bond. Each bond test tool is mounted to a load cell provided with a force transducer and associated electronics.

While there are a variety of different test tools, the part of the machine used to position the test tool and move the test tool or bond during a test may be the same for each test tool. Accordingly, test tools have been designed to be removable from the rest of the machine so that they can be replaced with a different type of test tool or a test tool suitable for a different range of measurements or a different type of bond or test. It may be desirable to use several different test tools on a single substrate under test and so an operator may be required to perform replacement of test tools frequently.

The requirement to be able to measure small forces accurately leads to certain requirements for the performance of each test tool. Shear test tools are used to shear a bond off a substrate and the force required to shear the bond is recorded. A force transducer is coupled to the shear test tool in order to measure the force. In order to ensure repeatability for shear measurements, it is essential for the tip of the test tool to engage the side of the bond at a predetermined height above the surface of the substrate. This distance is small but critical, since the bond is usually dome-shaped. A predetermined spacing from the surface eliminates both sliding friction from the test tool on the substrate, and ensures that the shear load is applied at a precise location in relation to the bond interface. Accordingly, in practice, the test tool is first moved into contact with the substrate surface and then withdrawn by a predetermined distance, typically 0.05 mm or less before the shear test is performed.

Several difficulties arise. Friction and stiction in the mechanism of the device itself may cause difficulties in sensing contact with the substrate surface. Imprecise surface sensing will inevitably affect the distance by which the test tool is withdrawn, and thus the height at which the bond is sheared. The distances involved are very small and so care needs to be taken to sense the exact moment of surface contact, without compression of the substrate. Care must also be taken to prevent uncontrolled movement of the test tool at the test height prior to or during the shear test. Such movement may seriously affect the accuracy of the test results and significant movement of the test tool at the test height may damage an adjacent bond or wire.

The twin objectives of both a low contact force when sensing the surface of the substrate and accurate control of the test height are difficult to resolve.

U.S. Pat. No. 6,078,387 discloses a device for sensing contact of a test head of a test tool with the substrate which is adapted to immediately stop downward drive of the test head when contact is sensed. The test tool is supported on the free end of a pair of parallel flexures, which are secured at their opposite ends to a base plate and deflect to allow some vertical movement of the test head with respect to the base plate. To prevent vertical movement of the test head during the shear tests, the test tool is spring biased by the flexures against the base plate. The test head can be moved away from the base plate by an air-bearing to allow the test head to move vertically in a substantially frictionless manner for initial contact sensing. Thus, when the test head first touches the substrate surface, it is pushed back by the substrate surface on the flexures. Movement of the test head relative to the base plate or movement of the flexure can be detected by an optical detector, and the air-bearing is then switched off to ensure that the test head is fixed relative to the base plate by the spring bias of the flexures against the base plate. Once the test head is fixed relative to the base plate, the base plate is raised by a predetermined amount so as to leave a clearance between the lower end of the test tool and the substrate of the desired "step off distance".

An alternative system is to have the parallel flexures bias the test tool away from the base plate to allow for substantially friction-free movement of the test head relative to the base plate during initial positioning, but then to press the test tool into contact with the base plate using a piston driven by compressed air to create a clamping force on the test tool against the base plate during a test procedure. A further alternative, described in EP2363701A, is to have the flexures bias the test tool away from the base plate to allow for substantially friction-free movement of the test head relative to the base plate during initial positioning, but then to clamp the test tool against an abutment fixed to the base plate using a piston driven by compressed air. The abutment may be complemented by a further abutment positioned to provide an additional clamping force during a shear test.

In all these alternatives, the use of flexures provides the ability to sense the surface of the substrate without damaging the substrate. The test tool is then prevented from movement relative to the base plate by a pneumatically operated clamp.

Pull and push testing typically use hook or jaw tools and requires a different configuration for the load cell. However, the tools may also employ a pair of parallel flexures, with one or more strain gauges positioned on the flexures to detect the force applied in a vertical direction. The flexures must be highly compliant in order to control the loading rate on the bond and to minimise damage due to accidental contact with the substrate. An example of this type of pull testing tool is described in U.S. Pat. No. 6,301,971B1.

While the machines described offer excellent measurement of the force needed to break a bond, it would be desirable to improve the ease of use of the machines. In particular, it would be desirable to improve the ability to switch between different test tools while retaining a high accuracy of measurement. It would also be desirable to be able to make such an improvement possible for existing machines.

SUMMARY OF THE INVENTION

In a first aspect of the invention, there is provided a cartridge configured to be removably coupled to a moving assembly of a bond testing machine, the cartridge comprising:

- a plurality of a different test tool assemblies;
- a rotary mechanism, each of the plurality of different test tool assemblies mounted to the rotary mechanism angularly spaced from one another;
- a drive unit, coupled to the rotary mechanism, the drive unit configured to rotate the rotary mechanism to move each of the plurality of different test tool assemblies to and from a use position; and
- an air interface for receiving compressed air from a corresponding air interface on the moving assembly of the bond testing machine.

Providing a plurality of test tool assemblies that can be selectively moved to a use position within a single cartridge allows an operator to change tools without having to demount and remount different test tool cartridges every time a different test tool is required. This improves the ease of operation and saves the operator time. The test tool assemblies are rotated by the rotary mechanism so that each test tool can be moved to and from a use position. The test tool assemblies may be fixed relative to one another so that all of the test tool assemblies rotate simultaneously, with, at most, only a single test tool assembly being in a use position at any one time.

Providing a rotary mechanism and drive unit within the cartridge allows the interchangeable test tool arrangement to be retrofitted to existing bond testing machines. The air interface allows the use of pneumatic clamping mechanisms for high accuracy positioning and measurement, particularly for shear test tools.

The cartridge is configured to be removably coupled to a bond testing machine, preferably in simple manner that can be performed manually without the need of special equipment. This allows the cartridge to be replaced by other multi-tool or single-tool cartridges as required.

As used herein, the term "test tool assembly" means a an assembly comprising a tool configured to perform a particular test, such as a pull test, push test or shear test, and a load cell for measuring a force applied during the test.

The rotary mechanism advantageously comprises an improved Geneva drive mechanism. A Geneva mechanism is a mechanism that transmits continuously rotating motion of a drive wheel into intermittent rotating motion of a driven wheel, typically using a pin and slot arrangement. The Geneva mechanism disclosed herein is believed to be an improvement over prior Geneva mechanism in the way it locks the driven wheel in desired position. The Geneva drive mechanism may comprise a driven wheel movable between a plurality of use positions, and a drive wheel configured to move the driven wheel. The Geneva drive mechanism allows each of the test tool assemblies to be accurately driven to a use position, substantially eliminating the possibility of rotational positioning errors. The driven wheel and drive wheel may be configured to engage one another to restrain or prevent movement of the driven wheel out of a use position when the drive wheel is stationary. The driven wheel may advantageously comprise a least one, and advantageously at least two, resilient elements in frictional engagement with the drive wheel to prevent the drive wheel undesirably rotating in either direction. Each resilient element may comprise a flexure or leaf spring.

The cartridge may further comprise control circuitry connected to the drive unit, wherein the control circuitry is configured to control the drive unit to decelerate the rotation of a drive wheel in the rotary mechanism as each test tool assembly approaches a use position. This deceleration of the drive wheel reduces vibration of the test tool as it is brought to the use position. This is particularly advantageous with the use of a Geneva drive mechanism as, for a large part of the rotation of the drive wheel, the driven wheel is not rotated. This part of the rotation of the drive wheel is advantageously done as quickly as possible. When the drive wheel engages a slot in the driven wheel to rotate the driven wheel, the rate of rotation of the driven wheel is advantageously progressively reduced until a use position for one of the test tool assemblies is reached.

The cartridge may further comprise an orientation detector configured to detect an orientation of the driven wheel and so the orientation of the test tools. This allows the control circuitry to establish when a test tool (and which test tool) is in the use position. The orientation detector may comprise a MEMS accelerometer mounted to the driven wheel and may be fixed on a circuit board mounted to the driven wheel.

The cartridge may further comprise a position detector configured to detect a position of one or more of the test tool assemblies. The position detector may comprise a photo interrupter.

The plurality of different test tool assemblies may comprise any combination of test tool assemblies. In some embodiments, the cartridge may include a shear test tool assembly and a pull test tool assembly. The plurality of different test tool assemblies may include a plurality of shear test tools and may further comprise a piston and cylinder, the piston and cylinder configured to operate a clamping mechanism in each shear test toot assembly. The clamping mechanism may be of the type described in EP2363701 A, the contents of which are incorporated herein by reference. Alternatively, a piston and cylinder may be provided in the bond testing machine outside of the cartridge. One or more of the test tool assemblies may comprise an air bearing using compressed air. A suitable air bearing is described in U.S. Pat. No. 6,078,387, the contents of which are incorporated herein by reference.

Each of the test tool assemblies is advantageously removably mounted to a cartridge main body. Different test tool assemblies may be substituted into the cartridge to meet specific operator requirements. The cartridge main body may include a mounting plate having two identical test tool connection areas, wherein two different test tool assemblies can be mounted at either of the two identical test tool connection areas.

The cartridge preferably comprises a housing, wherein the housing covers each test tool assembly that is not in a use position. This protects the test tool assemblies that are not in the use position. The cartridge may be configured such that in one position, the housing covers all of the test tool assemblies. This provides protection for all of the test tools when the cartridge is not in use, and is particularly advantageous during storage and transport of the cartridge.

One or more of the test tool assemblies may comprise a test tool mounted to a base plate by one or more flexures. In the case of a push or pull test tool, the flexures may comprise a force measurement transducer. In one embodiment, strain gauges on the flexures are used to measure the strain in the flexures as a result of a pull or push test. In the case of a shear test tool, the test tool may comprise a force measurement transducer. The flexures in a shear test tool assembly are provided to ensure a low touch down force on the substrate under test.

The cartridge main body may include a mounting plate for the test tools that includes an electrical power and data connection. The electrical power and data connection may be connected to a flexible electronic conductor that permits the mounting plate to rotate while maintaining an electrical connection through the flexible electronic conductor.

The cartridge may further comprise a photo-interrupter that is provided to sense when the driven wheel of the rotary drive mechanism reaches a locked position corresponding to a use position of one of the test tools. A flag feature may be provided that is detected by the photo-interrupter.

The cartridge may be configured to send feedback to the bond testing machine regarding which tool is in the use position so that bond testing machine can, in response, switch a compressed air supply on or off as appropriate to suit the test tool in use.

In a second aspect of the invention there is provided a cartridge suitable for use in a bond testing machine, the cartridge comprising:
  a plurality of a different test tool assemblies suitable for use in a bond testing machine, at least two of the test tools assemblies each comprising a test tool movably mounted to a base plate and comprising a pneumatic or hydraulic clamping mechanism either operable to clamp the test tool to the base plate or operable to release the test tool from the base plate; and
  a piston and cylinder, the piston and cylinder configured to operate each of the clamping mechanisms in the test tool assemblies.

In a third aspect of the invention, there is provided a cartridge suitable for use in a bond testing machine, the cartridge comprising:
  a plurality of a different test tool assemblies;
  a Geneva drive mechanism, each of the plurality of different test tool assemblies mounted to the Geneva mechanism and angularly spaced from one another;
  a drive unit, coupled to the Geneva drive mechanism, the drive unit configured to rotate the Geneva mechanism to move each of the plurality of different test tool assemblies to and from a use position.

In a fourth aspect of the invention, there is provided a bond testing tool comprising
  a cartridge in accordance with any one of the first to fourth aspects of the invention;
  a stage table configured to receive objects to be tested; and
  a moving assembly coupled to the stage table, the cartridge being mounted to the moving assembly; wherein the moving assembly is operable to position and move the cartridge relative to the stage table.

Preferably, the cartridge is mounted to the moving assembly such that, in use, the driven wheel of the cartridge is driven to rotate about a horizontal axis of rotation. Each of the test tools can then each be rotated to the same use position above a substrate on the stage table.

Advantageously, the cartridge is removably mounted to the moving assembly. The moving assembly may comprise a compressed air supply configured to supply compressed air to the cartridge to operate one or more clamping mechanisms in the cartridge.

In a fifth aspect of the invention, there is provided a Geneva drive mechanism comprising a driven wheel movable between a plurality of use positions, and a drive wheel configured to move the driven wheel, wherein the driven wheel comprises a least one resilient element in frictional engagement with the drive wheel and configured to restrain movement of the driven wheel out of an indexed position when the drive wheel is stationary.

Advantageously, the driven wheel comprises at least two resilient elements in frictional engagement with the drive wheel. Each resilient element may comprise a compliant beam extending from the driven wheel, the complaint beam configured at its free end to be urged into contact with a surface of the drive wheel. The force applied by the resilient arm on the drive wheel may be directed against a bearing surface on the drive wheel and advantageously in a radial direction with respect to the drive wheel. In this manner, it is possible to load the driven wheel against the drive wheel to obtain zero backlash in each position, meaning that driven wheel can be locked in the desired position with respect to the drive wheel when the drive wheel is stopped.

The drive wheel may comprise an engagement pin configured to engage one or more slots in the driven wheel in order to move the driven wheel between a plurality of indexed positions. The bearing surface may be configured to be out of engagement with the resilient arm when the engagement pin is engaged with a slot in the driven wheel.

Although the Geneva drive mechanism of this aspect of the invention is described herein with reference to a bond testing machine, it should be clear that it may equally be used in other machines to perform other functions, and may be particularly beneficial where existing solutions suffer from backlash.

In a sixth aspect of the invention, there is provided a bond testing system, the system comprising:
  a plurality of a different test tool assemblies,
  a rotary mechanism, each of the plurality of different test tool assemblies mounted to the rotary mechanism being angularly spaced from one another;
  a drive unit, coupled to the rotary mechanism, the drive unit configured to rotate the rotary mechanism to move each of the plurality of different test tool assemblies to and from a use position; and
  a orientation detector configured to detect an orientation of one or more of the test tool assemblies to determine when the test tool is in the use position, wherein the orientation detector is an accelerometer coupled to the test tool assembly or a photo-interrupter coupled to the rotary mechanism, or a combination of an accelerometer coupled to the test tool assembly and a photo-interrupter coupled to the rotary mechanism.

In a seventh aspect of the invention, there is provided a method of operating a bond testing system, the system comprising a plurality of a different test tool assemblies, a rotary mechanism, each of the plurality of different test tool assemblies mounted to the rotary mechanism being angularly spaced from one another; and a drive unit, coupled to the rotary mechanism, the drive unit configured to rotate the rotary mechanism to move each of the plurality of different test tool assemblies to and from a use position, the method comprising:

operating the rotary mechanism to move the plurality of test tool assemblies; and determining that a selected test tool assembly is in the use position based on a signals from a sensor The sensor may be an accelerometer coupled to the test tool assembly or a photo-interrupter coupled to the rotary mechanism.

The test tool assemblies can each be mounted in a plurality of positions on a test tool mount on the rotary mechanism, and the method may further comprise determining a position of each of the test tool assemblies on the test tool mount based on information stored on a memory storage device coupled to the test tool mount.

In an eighth aspect of the invention there is provided a method of operating a bond testing cartridge, the cartridge comprising a plurality of a different test tool assemblies suitable for use in a bond testing machine, at least two of the test tools assemblies each comprising a test tool movably mounted to a base plate and comprising a pneumatic or hydraulic clamping mechanism either operable to clamp the test tool to the base plate or operable to release the test toot from the base plate; and a piston and cylinder, the piston and cylinder configured to operate each of the clamping mechanisms in the test tool assemblies, the method comprising:

receiving feedback regarding which of the test tool assemblies is in a use position; and operating the piston and cylinder dependent on the feedback to suit the test tool assembly in the use position.

In a ninth aspect of the invention, there is provided a method of operating a bond testing machine comprising:

mounting a multi-tool cartridge, having a first test tool and a second test tool, to the bond testing machine by sliding the cartridge into engagement with a corresponding interface on the bond testing machine, so that an electronic interface and a compressed air interface of the cartridge mate with the corresponding interfaces on the bond testing machine;

selecting a first type test to be performed by the bond testing machine;

determining the position of the test tools within the cartridge by reading information from a memory device that stores the position of the test tools within the cartridge;

based on the information read from the memory device, rotating the first test tool from a non-use position within the housing of the cartridge to a use position to perform a first type of test;

performing the first type of test using the first test tool;

selecting a second type of test to be performed using the bond testing machine;

based on the information read from the memory device, rotating the first test tool from the use position to a non-use position within the housing while rotating the second test tool from a non-use position within the housing to a use position to perform a second type of test; and performing the second type of test using the second test tool Signals from a photo-interrupter or accelerometer may be used to determine when the first and second test tools are in the use position.

The method may further comprise the step of demounting the cartridge from the bond testing machine and mounting a single tool cartridge to the bond testing machine to perform a test using the single tool cartridge, Features described with reference to one aspect of the invention may equally be applied to other aspects of the invention. In particular, it should be clear that features described in relation to the first aspect of the invention may be applied to the second, third and sixth aspects of the invention, and features described in relation to the eighth and ninth aspects of the invention may be applied to the seventh aspect of the invention.

BRIEF DESCRIPTION OF THE DRAWINGS

Embodiments of the invention will now be described in detail, by way of example only, with reference to the accompanying drawings, in which:

FIG. 2a is an underside perspective view of a cartridge in accordance with the invention;

FIG. 2b is a side view of the cartridge of FIG. 2a;

FIG. 3b is a rear view of the cartridge of FIG. 3a;

DETAILED DESCRIPTION

Figure 1:
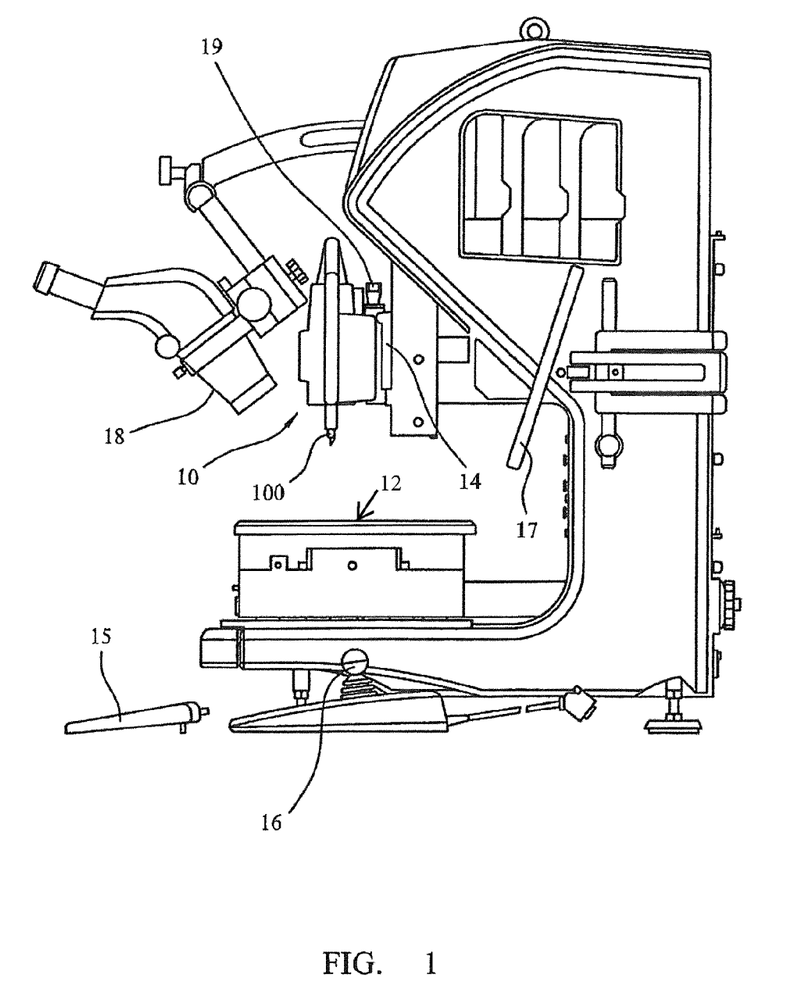
FIG. 1 is a side view of a bond testing machine in accordance with the invention.

FIG. 1 is an illustration of a bond testing machine in accordance with the present invention. The machine comprises a cartridge 10 containing a plurality of test tool assemblies 100 (only one of which is visible in FIG. 1), which is mounted to the moving assembly 14 of the device. Beneath the test tool assemblies 100 is a motorised stage table 12, on which samples to be tested can be mounted. The samples are typically substrates upon which solder ball deposits and wire bonds are formed to connect electronic components on the substrate.

The cartridge 10 is moveable in a direction normal to the sample, hereafter referred to as the Z-direction or axial direction, by the moving assembly 14. This allows the test tool assemblies to be positioned relative to the sample and provides the movement necessary for a pull test or to position the tool for a shear test. The moving assembly 14 that supports cartridge 10 is mounted to a ball screw, or lead screw and nut (not shown), and can be driven by an axial drive mechanism such as a servo motor or stepper motor (not shown), or any other suitable, controllable drive arrangement as is well known in the prior art. See, for example, the 4000Plus Bond Tester available from Dage Precision Industries Ltd, 25 Faraday Road, Rabans Lane Industrial Area, Aylesbury, Buckinghamshire, United Kingdom.

The stage table 12 is movable parallel to the plane of a sample under test, herein after referred to as the X-Y plane. This allows ball deposits to be moved along a test direction axis in a test direction towards and past a shear test tool during a shear test procedure. Movement of the stage table 12 is achieved using suitable servo motors or stepper motors coupled to the table via a leadscrew and nut, ballscrew and nut or suitable belt drive mechanism, as is also well known in the prior art such as the Dage 4000Plus Multipurpose Bond Tester referenced above.

Also shown in FIG. 1 are joystick controls 16 for controlling the movement of the stage table 12, and a keyboard 15. A display 17 and a microscope 18, for aiding accurate positioning of the test tool, are also shown. These features are also all well known in the prior art such as the Dage 4000Plus Multipurpose Bond Tester available from Dage Precision Industries Limited.

Figures 2A, 2B:
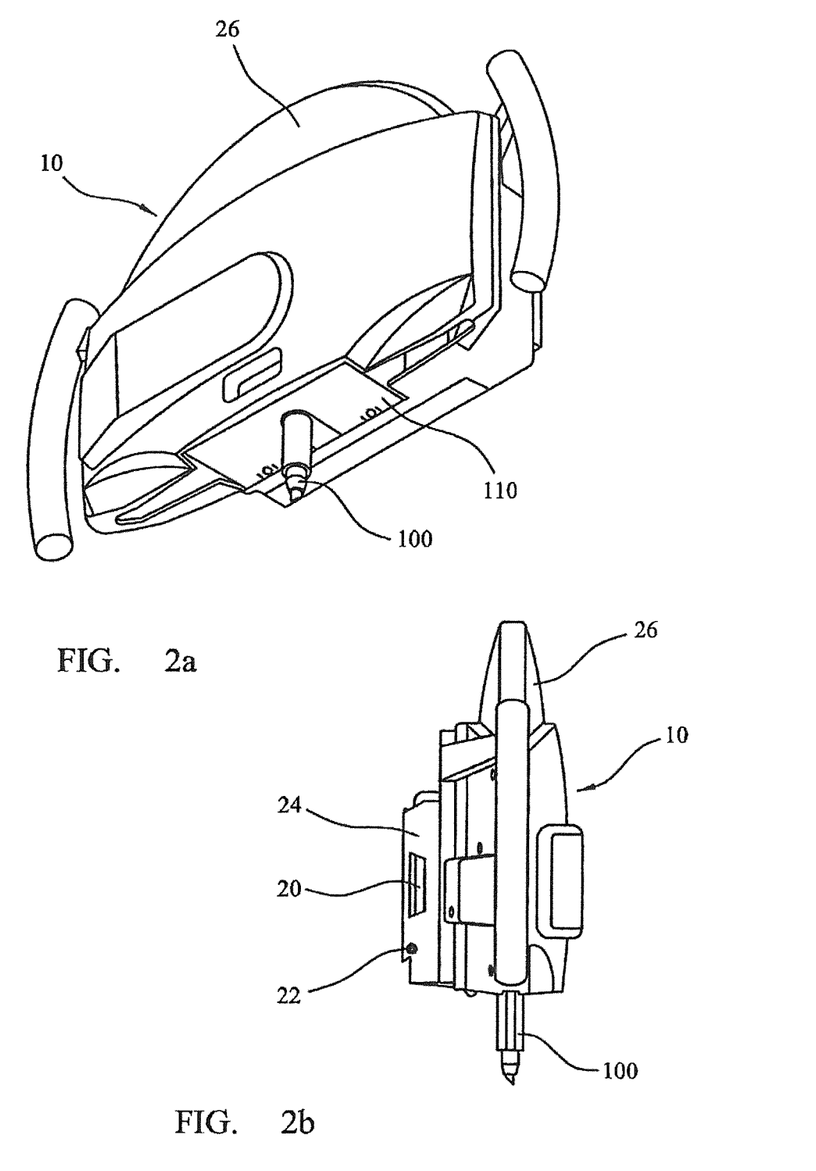

FIG. 2a shows an underside perspective view of the cartridge 10. The cartridge has an outer housing 26 that covers a test tool mount or mounting plate 110 that holds three test tool assemblies. One test tool assembly 100 is shown in a use position, extending out of the housing 26. As will be described in detail, the test tool assembly is able to rotate within the housing 26 to move the test tools between non-use positions and the use position.

FIG. 2b is a side view of the cartridge of FIG. 2a. It can be seen from FIG. 2b that the cartridge includes an electrical interface 20 and a compressed air interface 22 formed in a mounting portion 24 of the housing 26. The mounting portion 24 of the housing is configured to be mounted to the moving assembly 14 of the machine. Any suitable mounting interface may be used. In this embodiment the mounting portion 24 is configured to slide into engagement with a corresponding interface on the bond testing machine, so that the electronic interface 20 and compressed air interface 22 mate with the corresponding interfaces on the bond testing machine. Once the cartridge is fully engaged with the bond testing machine it is clamped in position by manually tightening screw 19. Desirably, the cartridge is configured to be mountable to positioning assemblies, also referred to as a moving assembly, of pre-existing bond testing machines as a retrofit bond testing tool assembly.

Figure 2C:
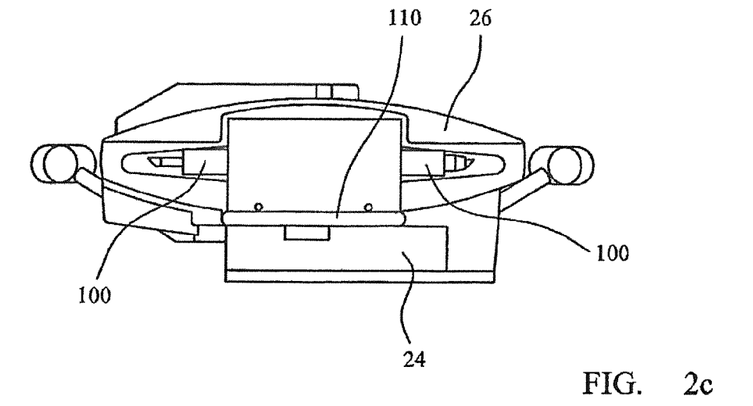
FIG. 2c is an underside view of the cartridge of FIG. 2a, in non-use configuration.

FIG. 2c is an underside view of the cartridge of FIG. 2a, in non-use configuration. The test tool mount 110 has been rotated within the housing 26 to a storage position in which none of the test tools 100 are in a use position and all the test tool assemblies are covered by the housing 26. This is useful during transport and storage.

Figure 3A:
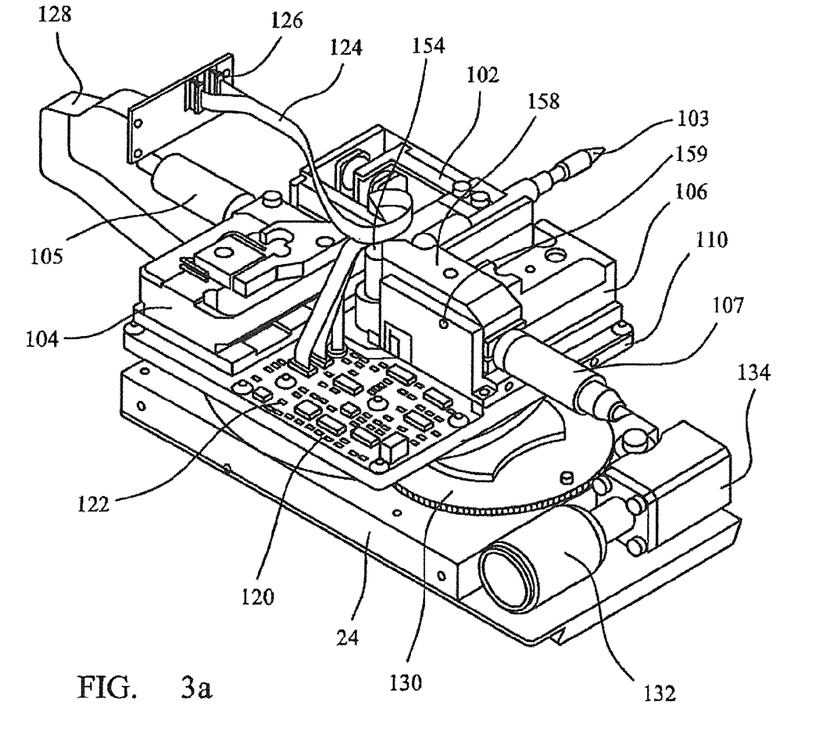
FIG. 3a is a front perspective view of the cartridge of FIG. 2a, with the outer housing removed.

FIG. 3a is a front perspective view of the cartridge of FIG. 2a, with the outer housing removed. The mounting portion 24 supports the test tool mount on a Geneva drive mechanism. The three separate test tool assemblies can be clearly seen. Pull tool assembly 102, first shear tool assembly 104 and second shear tool assembly 106 are each fixed to the test tool mount 110. Each test tool assembly comprises a test tool 103, 105, 107, which extends radially outward from the axis of rotation of the test tool mount. Each test tool is supported on the free end of a pair of flexures, which are secured to a base plate. The test tools are typically bolted to the free ends of the flexures. The flexures are typically machined from a single piece and include openings through which bolts can pass to secure the test tools. The flexures deflect to allow some vertical movement of the test head with respect to the base plate. The pull test tool assembly is of the type described in U.S. Pat. No. 6,301,971. The shear test tool assemblies are of the type described in U.S. Pat. No. 6,078,387 and EP2363701. But it should be clear that any combination of test tool assemblies may be used in the cartridge. Electronic circuitry 120 is fixed to the test tool mount 110. The electronic circuitry 120 is configured to receive and process signals from the test heads 103, 105, 107 and output signals to the electronics interface 20. The electronic circuitry also includes a MEMS accelerometer 122 which is used to determine the orientation of the mount and so the orientation of the test tools. This allows the control circuitry to establish when a test tool (and which test tool) is in the use position. This information is provided to control circuitry in the positioning assembly through the electronics interface 20 so that the supply of compressed air can be appropriately controlled and so that the measurement data can be appropriately interpreted.

Figure 3B:
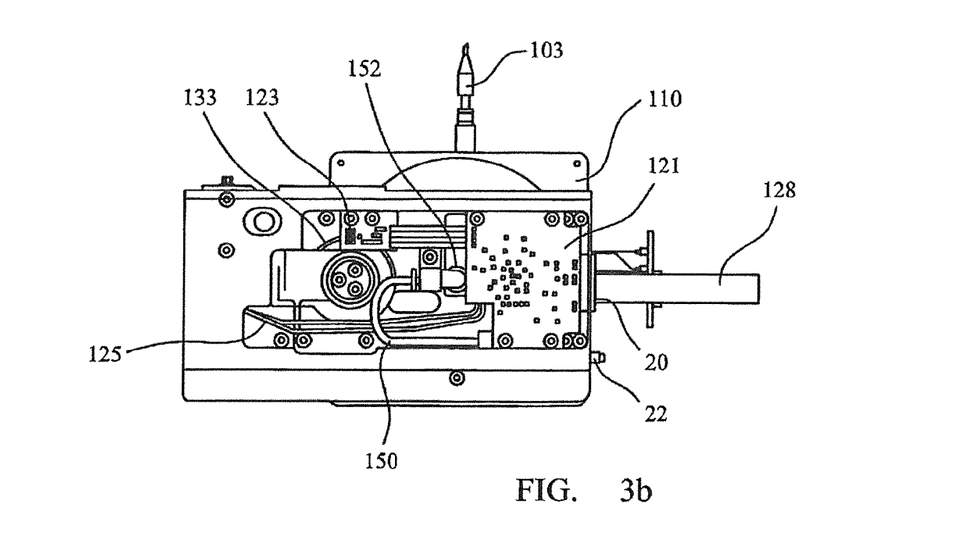

Electrical power and data connection to the test tool mount 110 from the mounting portion 24 of the cartridge is provided by flexible electronic connections 124 and connection 128, through intermediate connector board 126. FIG. 3b is a rear view of the cartridge of FIG. 3a. Circuit board 120, shown in FIG. 3b, is connected to the electronics interface 20. Connection 128 is fixed at one end to circuit board 120 and at the other to intermediate connector board 126. Flexible connections 124 are fixed at one end to the intermediate connector board 126 and at the other to circuit board 122. Connection 128 is shaped to provide clearance for the test tools to rotate. The flexible connections 124 permit the test tool mount110 to rotate relative to the mounting portion 24 while maintaining an electrical connection.

Figure 4:
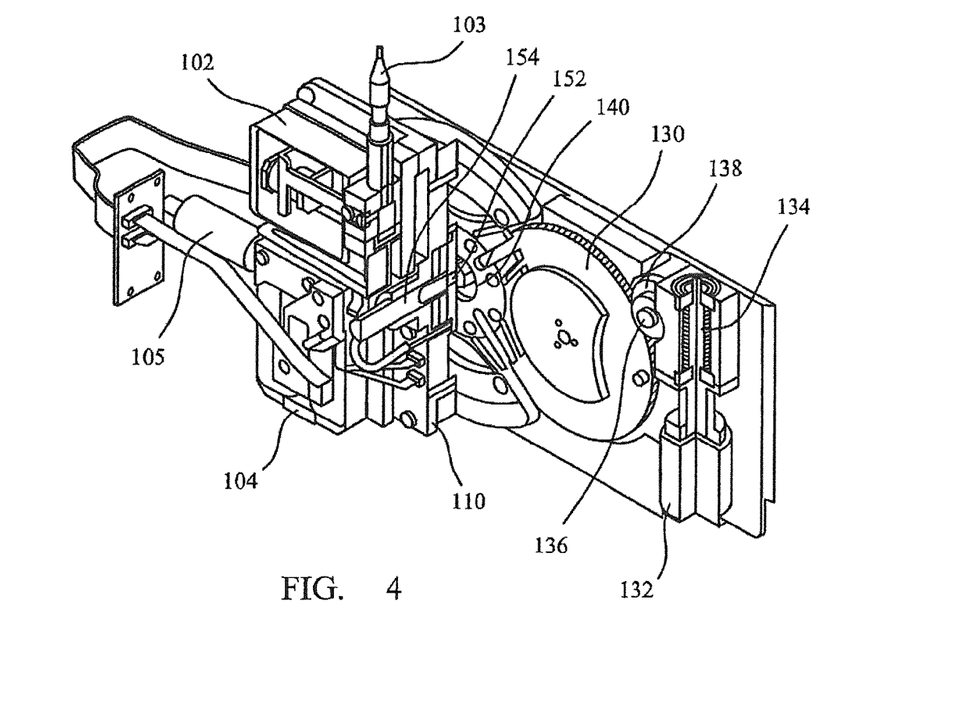
FIG. 4 shows the cartridge of FIG. 3a, with a portion of the test tool assembly cut away to reveal the rotation mechanism.
Figure 5:
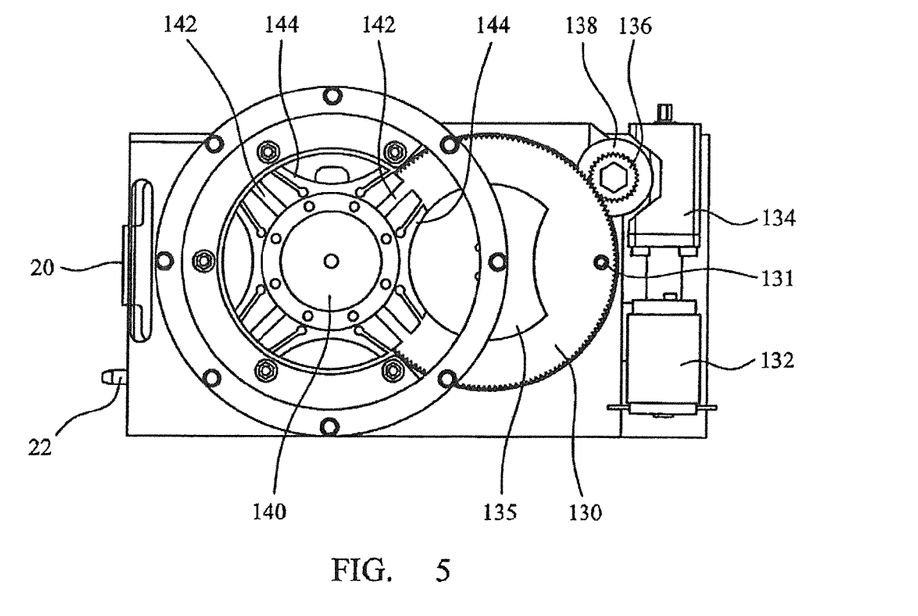
FIG. 5 illustrates the rotation mechanism of the cartridge of FIG. 4.

Compressed air interface 22 connects to air input tube 150. Air input tube 150 is connected to a rotary fitting 152 around the axis of rotation of the test tool mount 110. Electrical power is supplied to the motor 132 from electrical interface 20 through mounting portion circuit board 121 and then through wires 125. The rotary drive mechanism for the test tool assemblies is a Geneva drive mechanism. This is mostly clearly illustrated in FIGS. 4 and 5. FIG. 4 shows the cartridge of FIG. 3a, with a portion of the test tool mount cut away to reveal the rotation mechanism. FIG. 5 illustrates the rotation mechanism of the cartridge of FIG. 4 with the test tool assemblies and test tool mount removed entirely.

Referring to FIG. 5, the Geneva drive mechanism comprises a motor 132 driving a worm gear 134 (which is shown partially cut away in FIG. 4). The worm gear engages a worm wheel 138 to which a spur gear 136 is mounted. The spur wheel 136 engages a drive wheel 130 of the Geneva drive mechanism. The drive wheel 130 comprises a pin 131 configured to engage a driven wheel 140 of the Geneva drive mechanism. The driven wheel 140 comprises a plurality of equally spaced slots 142 into which the pin 131 can pass. When the pin 131 enters a slot 142 it engages the driven wheel 140 and, as the drive wheel rotates, the driven wheel rotates. After 90 degrees of rotation, the pin 131 leaves the slot 142, after which rotation of the drive wheel does not cause any further rotation of the driven wheel until the pin 131 enters the next slot 142. Each full turn of the drive wheel 130 results in a quarter turn of the driven wheel 140. The motor 132 is controlled so that the drive wheel is rotated relatively quickly for the period of rotation in which the pin 131 is not engaged with the driven wheel and then slowed for the period of rotation in which the pin 131 is engaged with the driven wheel. Slow rotation of the driven wheel is advantageous as it reduced vibration of the test tools attached to the driven wheel, which can affect measurement accuracy. Control of the motor is provided by the mounting portion circuit board 121, which also receives orientation data from the accelerometer 122 and photo-interrupter 123.

In this embodiment, there are four slots 142 in the driven wheel to provide four discrete locked positions for the driven wheel. This provides three use positions, one for each test tool, and a storage position in which all of the test tools are held within the housing 26. However, it should be clear that any number of slots may be chosen. Similarly, more than one pin 131 may be provided on the drive wheel 130 so that the driven wheel is moved to a new position a plurality of times for each full rotation of the drive wheel.

In order to prevent or minimise any movement of the driven wheel when the pin 131 is not engaged in a slot 142 and the drive wheel is stationary, the driven wheel includes a plurality of arcuate resilient beams 144, shaped to engage a bearing surface 135 on the drive wheel 130. The resilient beams 144 and bearing surface 135 are shaped to prevent movement of the driven wheel until the pin 131 engages a slot 142. In particular, the bearing surface extends around 270 degrees of rotation. The resilient beams are flexible to ensure a frictional engagement with the bearing surface 135, to lock the driven wheel in position and eliminate any clearance that might allow the driven wheel to wobble. In particular, the resilient beams 144 are configured to engage the bearing surface at their free ends, with a clearance existing between the bearing surface and the fixed ends of the resilient arms. By carefully setting the position of the rotation axes of the drive wheel and the driven wheel it is possible to preload the driven wheel to obtain zero backlash in each position of the driven wheel. This ensures that the test tools attached to drive wheel will always be positioned in the same, desired position when the indexed to the use position.

A photo-interrupter 123, shown in FIG. 3b, is provided to sense when the driven wheel of the rotary drive mechanism reaches a locked position. A flag feature that is detected by the photo-interrupter is provided on the back face of the drive wheel. The flag feature is a ridge 133 that extends for 180 degrees of the drive wheel, which corresponds to the engagement of the two resilient beams contacting the drive wheel. The photo-interrupter 123 is arranged so that the ridge interrupts a light beam. Information from the photo-interrupter, together with information from accelerometer 122, is used to determine that a test procedure can begin.

Providing the rotary mechanism within the cartridge rather than within the machine to which cartridges are mounted, allows for the same machine to be used with multi-tool cartridges and single tool cartridges that do not require rotation and keeps the cost of the machine lower, particularly for those customers that do not need multi-tool cartridges. Furthermore, housing the rotary mechanism within the cartridge simplifies the interface between the machine and cartridge. Only an electrical interface and a compressed air interface are required.

FIG. 4 shows the cartridge of FIG. 3a, with a portion of the test tool mount cut away. It can be seen that the mount 110 is simply fastened to the driven wheel of the Geneva drive mechanism. The compressed air is delivered through rotary mounting 152 to both the connecting tube 156 for those test tool assemblies having an air bearing mechanism and to the piston 154 for those test tool assemblies having a pneumatic clamping mechanism.

Shear test tool assembly 106 has a clamping mechanism of the type described in EP2363701A. A piston and cylinder 154 is provided to operate a clamping lever in the test tool assembly 106 to hold the test tool 107 in a fixed position relative to the base plate during a shear test. A secondary lever 158 is provided, magnifying the force applied by the piston 154 and reducing the stroke at the clamp site. The secondary lever has a first end that acts on the clamping lever and a second end that is acted on by the by the piston 154. The secondary lever pivots about a pin 159 that is attached to the base plate at either end. The pin is located closer to the second end of the secondary lever than the first end, and so the second end of the lever moves through a shorter path than the first end. This reduces the length of stroke required of the piston 154 to produce a given movement of the clamping lever onto the test tool 107. The piston and cylinder 154 can be used to operate a plurality of clamps in different test tool assemblies.

Air for the piston and cylinder, and for an air bearing in shear test tool assembly 104, is controlled and switched from the positioning assembly of the bond test machine. Different types of clamping arrangements require different control. Air bearing type assemblies of the type described in U.S. Pat. No. 6,078,387A use air ON to release the clamp, air OFF to clamp. Clamp type assemblies of the type described in EP2363701A use air ON to clamp, air OFF to release the clamp. The bond test machine receives feedback from the test tool mount, and in particular, from accelerometer 122, regarding which tool is in the use position. A controller in the positioning assembly can therefore switch the air supply on or off to suit the test tool in use.

Figure 6:
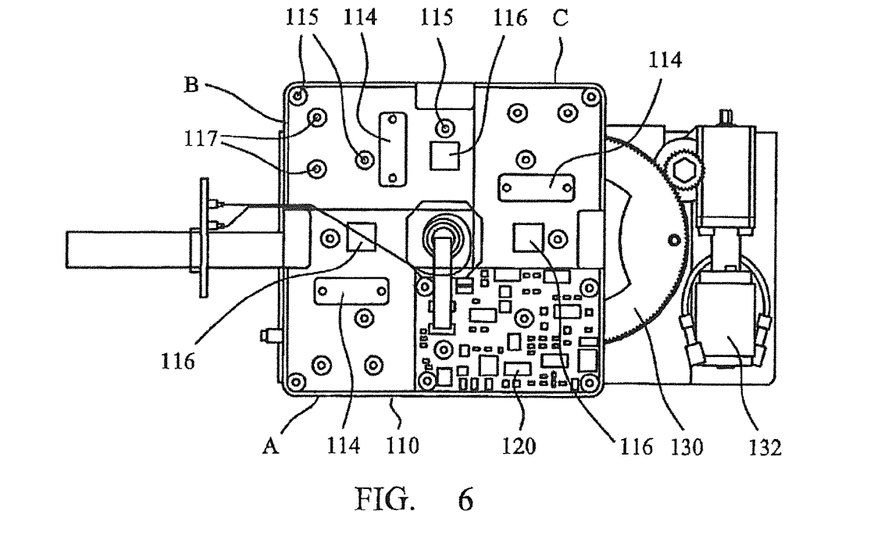
FIG. 6 shows the cartridge of FIG. 2a with the test tools removed

FIG. 6 shows the cartridge of FIG. 2a with the test tool assemblies removed. It can be seen from FIG. 6 that the test tool assemblies are simply bolted to the mounting plate 110 using mechanical fastenings 114. Electrical connections between each test tool and the mounting plate are made through interfaces 116. Each transducer assembly has connections in a common position.

Common connector positions enable test tool assemblies to be interchanged. Each test tool assembly also shares common mounting fixing holes and location dowels. Thus, the mounting plate 110 is comprised of a central hub, surrounded by three identical test tool connection areas A, B, C and one electronic circuitry area 120. Starting from connection area A and moving in a counterclockwise direction in FIG. 6, each of the tool connection areas is rotated 90° with respect to the other. Each has an electrical interface 116, a mechanical fastening element 114, fixing holes 115 and location dowels 117 that are positioned in identical locations. This means that any of the test tools can be mounted to any of the tool connection areas. Cartridges can be assembled with particular combinations of test tool assemblies to suit particular customer requirements. During assembly and set-up of the cartridge, typically in a manufacturing facility, a non-volatile memory device on the circuit board 120 in the cartridge is programmed with the type of each of the tools on the mounting plate 110, together with calibration values. Memory locations within the memory device are allocated for each mounting position on the mounting plate 110 so that the position of each of the test tool can be determined by reference to the memory location.

Having described the structure of the cartridge, its operation is as follows: The cartridge is mounted to the bond testing machine by sliding the mounting portion 24 into engagement with the corresponding interface on the bond testing machine, so that the electronic interface 20 and compressed air interface 22 mate with the corresponding interfaces on the bond testing machine. Once the cartridge is fully engaged with the bond testing machine it is clamped in position by manually tightening screw 19. Initially all three test tools are in a "parked" position i.e. a non-use position, within the outer housing 26 of the cartridge. When a user wishes to start a test, an object to be tested is first placed and secured to the stage table 12. The user then selects the type of test to be performed using keyboard 15 and display screen 17. The position of the test tools on the mounting plate is determined by the bond testing machine reading the memory device on the cartridge. The required test tool is then rotated to the use position, decelerating as it approaches the use position to minimise vibration. For example, for a pull test, the Geneva mechanism is operated rotate the mounting plate 110 to rotate the pull test tool 103 to the use position. Signals from both the photo-interrupter 123 and the accelerometer 122 are used to confirm when the pull test tool is in the use position. The pull test can then be performed. Using the joystick controls 16, the stage table is moved so that a particular bond to be tested is positioned underneath the test tool. The pull test is then performed using moving assembly 14. Strain gauges on the flexures are used to measure the force required to pull the bond off the underlying substrate.

If subsequently a shear test is to be performed, the user selects the type of shear test to be performed using keyboard 15 and display screen 17. The required shear test tool is then rotated to the use position by the mounting plate 110. Signals from the photo-interrupter 123 and the accelerometer 122 are used to determine when the shear test tool is in the use position. The user may use the joystick controls to move the stage table and correctly position a bond to be tested under the shear test tool. The shear test is then performed. Moving assembly 14 positions the tool vertically, using the flexures to sense contact of the tool with the substrate. The test tool then is locked to the base plate using an air bearing or pneumatic clamp as described in U.S. Pat. No. 6,078,387A and EP2363701A. The bond testing machine knows which type of clamping arrangement is on the test tool from the data stored in the memory device and turns the supply of compressed air to the air interface on or off as appropriate. Moving assembly then correctly positions the tip of the test tool a predetermined distance above the substrate. The stage table is then moved relative to the shear test tool to perform the shearing of the bond from the substrate. Strain gauges on the test tool measure the force exerted on the tool as the bond is sheared off the underlying substrate If a different test tool, not within the cartridge, is required, the cartridge can be demounted from the bond testing machine and a different cartridge, having the different required tool or tools, mounted in its place. To demount the cartridge, the screw 19 is loosened and cartridge slid out of engagement with the electrical interface and air interface on the moving assembly of the bond testing machine. A new cartridge can then be mounted to the moving assembly in the same manner. The new cartridge may be a multi-tool cartridge with a Geneva mechanism, as described, or may be a single tool cartridge without a rotary mechanism. The new cartridge interfaces with the electrical interface and air interface on the moving assembly of the bond testing machine in the same manner, and also has a memory device storing the type of tool or tools on the cartridge and associated calibration data.

With this arrangement, it is very simple to interchange cartridges when necessary, but cartridges with a plurality of tools may be used to allow different tests to be performed without changing the cartridge.

The invention claimed is:

1. A cartridge for a bond testing machine, the cartridge comprising:
 a plurality of different test tool assemblies;
 a rotary mechanism positioned within the cartridge, wherein each of the plurality of different test tool assemblies are mounted to the rotary mechanism and angularly spaced from one another;
 a drive unit coupled to the rotary mechanism, the drive unit configured to rotate the rotary mechanism to move each of the plurality of different test tool assemblies to and from a use position; and
 an air interface for receiving compressed air from a corresponding air interface on a moving assembly of the bond testing machine,
 wherein the cartridge is configured to be removably coupled to the moving assembly of the bond testing machine.

2. The cartridge according to claim 1, wherein the rotary mechanism includes a Geneva drive mechanism having a drive wheel and a driven wheel, and wherein constant rotation of the drive wheel causes intermittent rotation of the driven wheel.

3. The cartridge according to claim 2, wherein the driven wheel is movable between a plurality of use positions, and the drive wheel is configured to move the driven wheel, wherein a least one resilient element is in frictional engagement between the driven wheel and the drive wheel, and wherein said resilient element is configured to restrain movement of the driven wheel out of one of the plurality of use positions when the drive wheel is stationary.

4. The cartridge according to claim 2, further comprising a photo-interrupter that is configured to sense when the driven wheel of the Geneva drive mechanism reaches a locked position.

5. The cartridge according to claim 4, wherein a flag feature is provided that is detected by the photo-interrupter.

6. The cartridge according to claim 1, further comprising electronic circuitry connected to the drive unit, wherein the electronic circuitry is configured to control the drive unit to decelerate the rotation of a drive wheel in the rotary mechanism as each test tool approaches a use position.

7. The cartridge according to claim 1, further comprising an orientation detector configured to detect an orientation of one or more of the plurality of different test tool assemblies.

8. The cartridge according to claim 7, wherein the orientation detector comprises a MEMS accelerometer.

9. The cartridge according to claim 1, further comprising a position detector configured to detect a position of one or more of the plurality of different test tool assemblies.

10. The cartridge according to claim 1, wherein the plurality of different test tool assemblies includes a shear test tool assembly and a pull test tool assembly.

11. The cartridge according to claim 1, wherein at least one of the plurality of different test tool assemblies comprises an air bearing using compressed air.

12. The cartridge according to claim 1, wherein each of the plurality of different test tool assemblies is removably mounted to a cartridge main body.

13. The cartridge according to claim 12, wherein the cartridge main body includes a mounting plate having two identical test tool connection areas, and wherein two different test tool assemblies can be mounted at either of the two identical test tool connection areas.

14. The cartridge according to claim 13, wherein, in one position, the housing covers all of the of the plurality of different test tool assemblies.

15. The cartridge according to claim 1, further comprising a housing, wherein the housing covers each of the plurality of different test tool assemblies that is not in a use position.

16. The cartridge according to claim 1, wherein the cartridge includes a mounting plate for the plurality of different test tool assemblies, the mounting plate including an electrical power and data connection that is connected to a flexible electronic connection, the flexible electronic connection permitting the mounting plate to rotate while maintaining an electrical connection.

17. The cartridge according to claim 1, wherein the cartridge is configured to send feedback regarding which tool is in the use position so that the bond testing machine can switch a compressed air supply on or off to suit the test tool in use.

18. A bond testing tool, comprising:
 the cartridge according to claim 1;
 a stage table configured to receive objects to be tested; and a moving assembly coupled to the stage table, the cartridge being mounted to the moving assembly, wherein the moving assembly is configured to position and move the cartridge relative to the stage table.

19. A cartridge suitable for use in a bond testing machine, the cartridge comprising:
a plurality of different test tools;
a Geneva mechanism positioned within the cartridge, each of the plurality of different test tools mounted to the Geneva mechanism and angularly spaced from one another; and
a drive unit coupled to the Geneva mechanism, the drive unit configured to rotate the Geneva mechanism to move each of the plurality of different test tools to and from a use position.

20. A Geneva drive mechanism, comprising:
a driven wheel movable between a plurality of use positions, wherein the driven wheel comprises a plurality of slots and at least one resilient element; and
a drive wheel configured to engage the driven wheel, wherein the drive wheel comprises a pin,
wherein the driven wheel is rotated between the plurality of use positions by the drive wheel when the pin is engaged with at least one of the plurality of slots, and wherein the driven wheel is restrained from rotating out of one of the plurality of use positions when the at least one resilient element is frictionally engaged with the drive wheel and when the drive wheel is stationary.

21. A bond testing system, comprising:
a cartridge,
a plurality of different test tool assemblies,
a rotary mechanism positioned within the cartridge, each of the plurality of different test tool assemblies mounted to the rotary mechanism being angularly spaced from one another;
a drive unit coupled to the rotary mechanism, the drive unit configured to rotate the rotary mechanism to move each of the plurality of different test tool assemblies to and from a use position; and
an orientation detector configured to detect an orientation of one or more of the test tool assemblies to determine whether the test tool is in the use position, wherein the orientation detector is an accelerometer coupled to the test tool assembly or a photo-interrupter coupled to the rotary mechanism, or a combination of an accelerometer coupled to the test tool assembly and a photo-interrupter coupled to the rotary mechanism.

22. A method of operating a bond testing system, the bond testing system comprising a cartridge, a plurality of different test tool assemblies, a rotary mechanism, and a drive unit, coupled to the rotary mechanism, the drive unit configured to rotate the rotary mechanism to move each of the plurality of different test tool assemblies to and from a use position, the method comprising:
operating the rotary mechanism to move the plurality of different test tool assemblies, wherein the rotary mechanism is positioned within the cartridge, and wherein each of the plurality of different test tool assemblies is mounted to the rotary mechanism and is angularly spaced from one another; and
determining that a selected test tool assembly is in the use position based on a signal from a sensor.

23. The method according to claim 22, wherein the plurality of different test tool assemblies are mounted in a plurality of positions on a test tool mount on the rotary mechanism, the method further comprising determining a position of each of the plurality of different test tool assemblies on the test tool mount based on information stored on a memory storage device coupled to the test tool mount.

24. The method according to claim 22, wherein the sensor is an accelerometer coupled to the test tool assembly or a photo-interrupter coupled to the rotary mechanism.

25. A method of operating a bond testing cartridge, the bond testing cartridge comprising a plurality of a different test tool assemblies suitable for use in a bond testing machine, at least two of the test tools assemblies each comprising a test tool movably mounted to a base plate and comprising a pneumatic or hydraulic clamping mechanism either operable to clamp the test tool to the base plate or operable to release the test tool from the base plate; and a piston and cylinder, the piston and cylinder configured to operate each of the clamping mechanisms in the test tool assemblies, the method comprising:
receiving feedback regarding which of the test tool assemblies is in a use position; and
operating the piston and cylinder dependent on the feedback to suit the test tool assembly in the use position, wherein the piston and cylinder are both positioned within the bond testing cartridge.

26. A method of operating a bond testing machine, the method comprising:
mounting a multi-tool cartridge, comprising a first test tool and a second test tool, to the bond testing machine by sliding the cartridge into engagement with a corresponding interface on the bond testing machine, so that an electronic interface and a compressed air interface of the cartridge mate with the corresponding interfaces on the bond testing machine;
selecting a first type test to be performed by the bond testing machine;
determining the position of the test tools within the cartridge by reading information from a memory device that stores the position of the test tools within the cartridge;
based on the information read from the memory device, rotating the first test tool from a non-use position within the housing of the cartridge to a use position to perform a first type of test;
performing the first type of test using the first test tool;
selecting a second type of test to be performed using the bond testing machine;
based on the information read from the memory device, rotating the first test tool from the use position to a non-use position within the housing while rotating the second test tool from a non-use position within the housing to a use position to perform a second type of test; and
performing the second type of test using the second test tool.

27. The method according to claim 26, wherein signals from a photo-interrupter or accelerometer are used to determine when the first and second test tools are in the use position.

28. The method according to claim 26, further comprising demounting the cartridge from the bond testing machine and mounting a single tool cartridge to the bond testing machine to perform a test using the single tool cartridge.

* * * * *